(12) United States Patent
Alrowis et al.

(10) Patent No.: US 12,140,420 B1
(45) Date of Patent: Nov. 12, 2024

(54) SOFT TISSUE CALIPER

(71) Applicant: KING SAUD UNIVERSITY, Riyadh (SA)

(72) Inventors: Raed Mohamad Alrowis, Riyadh (SA); Zuhair Saleh Natto, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/655,638

(22) Filed: May 6, 2024

(51) Int. Cl.
*G01B 3/28* (2006.01)
*G01B 5/18* (2006.01)
*A61B 90/00* (2016.01)

(52) U.S. Cl.
CPC ............. *G01B 3/28* (2013.01); *G01B 5/18* (2013.01); *A61B 2090/062* (2016.02)

(58) Field of Classification Search
CPC ........ G01B 3/28; G01B 5/18; A61B 2090/062
See application file for complete search history.

(56) References Cited

U.S. PATENT DOCUMENTS

| | | | | |
|---|---|---|---|---|
| 4,033,043 A | * | 7/1977 | Cunningham | A61B 17/88 33/542 |
| 4,226,025 A | * | 10/1980 | Wheeler | G01B 3/166 600/587 |
| 4,233,743 A | * | 11/1980 | Flick | G01B 3/20 600/587 |
| 5,175,941 A | * | 1/1993 | Ziegler | G02C 13/003 33/200 |
| 6,263,585 B1 | * | 7/2001 | Dickinson | G01B 5/0004 33/783 |
| 6,887,250 B1 | | 5/2005 | Dority et al. | |
| 7,676,943 B2 | * | 3/2010 | Kim | A61B 90/06 33/512 |
| 8,512,349 B2 | * | 8/2013 | Mengato | A61B 90/06 33/512 |
| 8,875,408 B2 | * | 11/2014 | Steffensen | G01C 15/06 33/809 |
| 9,603,565 B2 | * | 3/2017 | Dell'Oca | A61F 2/4657 |
| 11,602,407 B2 | * | 3/2023 | Henry | A61B 90/06 |
| 2013/0152398 A1 | * | 6/2013 | Wagstaff | G01B 5/02 264/334 |

(Continued)

FOREIGN PATENT DOCUMENTS

CN 204421788 U 6/2015
CN 206618357 U 11/2017

(Continued)

*Primary Examiner* — Yaritza Guadalupe-McCall
(74) *Attorney, Agent, or Firm* — Nath, Goldberg & Meyer; Joshua B. Goldberg

(57) ABSTRACT

A soft tissue gauge includes a fixed probe for insertion into tissue to assess a depth of insertion of the fixed probe. The fixed probe has a fixed probe depth indicator to determine the depth of insertion of the fixed probe. A movable probe for insertion into tissue is also provided to assess a depth of insertion of the movable probe. The movable probe has a movable probe depth indicator to determine the depth of insertion of the movable probe. A ruler is provided having a fixed base supporting the fixed probe and a movable base supporting the movable probe. The movable base has a sliding part allowing for adjustment of the movable probe along the ruler to a desired length.

7 Claims, 1 Drawing Sheet

(56) References Cited

U.S. PATENT DOCUMENTS

2014/0059873 A1* 3/2014 Brookover ........... A61B 5/1072
33/512
2014/0325859 A1 11/2014 Plachtyna et al.
2018/0214234 A1* 8/2018 Henry .................... A61B 90/06
2022/0362036 A1* 11/2022 Rasmussen ............... A61F 2/38

FOREIGN PATENT DOCUMENTS

CN 207186620 U 4/2018
WO WO-2005027745 A1 * 3/2005 ............. A61B 17/88

* cited by examiner

SOFT TISSUE CALIPER

BACKGROUND

1. Field

The present disclosure relates to soft tissue grafts and particularly to oral grafts and skin grafts with different thicknesses and widths.

2. Description of the Related Art

Soft tissue grafts from a strip of tissue are usually performed in reconstructive surgery including gingival and dermal grafting. In daily practice, a clinician manually trims a harvested tissue to prepare a graft based on the desired size and thickness for implantation at a grafting site; Rijhwani et al., Free Gingival Autograft and Subepithelial Connective Tissue Graft for the Treatment of Gingival Recession: A Brief Review and Report of Three Cases. Seema Yadav Journal of Contemporary Dentistry, September-December 2016; 6(3):225-232; Harris R J. Creeping attachment associated with the connective tissue with partial-thickness double pedicle graft. J. Periodontol. 1997 September; 68(9): 890-9.

There are several types of oral soft tissue grafts such as free gingival grafts, connective tissue grafts, and pedicle grafts. These grafts are commonly obtained from an intraoral donor site such as the hard palate. Such grafts can be used to treat conditions such as multiple gum recession, exposed roots, teeth sensitivity, and increase keratinized tissue thickness; Rijhwani et al, 2016, supra. These conditions can occur due to several factors including periodontal disease, physiologic bone loss, trauma, heavy brushing, and incorrect tooth position; Dembowska E, et al., Subepithelial connective tissue graft in the treatment of multiple gingival recession. Oral Surg Oral Med Oral Pathol Oral Radiol Endod. 2007 September; 104(3):e1-7. Epub 2007 July 6; Rijhwani et al, 2016, supra; Wang L, et al., Refinement and Evaluation of Modified Minimally Invasive Harvest Technique for Subepithelial Connective Tissue. J Craniofac Surg. 2018 July; 29(5):1287-1290. Once there is an occurrence of one of these conditions, it can lead to uncomfortable sensations during eating or drinking hot or cold foods. The teeth can also become sensitive when exposed to air and are at a higher risk of caries due to difficulty in cleaning. Moreover, there may be a reduction in self-confidence and image due to an unaesthetic appearance.

Moreover, soft-tissue grafts are commonly used to reconstruct the anterior cruciate ligament with hamstring or fascia lata (deep fascia of the thigh) grafts. This area is a common place of ligament tearing during sports activities such as football or skiing; Wilde J, et al., Revision anterior cruciate ligament reconstruction. Sports Health. 2014 November; 6(6):504-18.

There are various techniques to obtain a soft tissue graft such as the trap-door technique described by Edel, A. Clinical evaluation of free connective tissue grafts used to increase the width of keratinized gingiva. J Clin Periodontol 1974; 1:185-96. The parallel incision is another technique. Subepithelial connective tissue graft technique for root coverage. J. Periodontol. 1985; 56:715-20. Other techniques include two crescent-shaped horizontal incisions: Raetzke P B. Covering localized areas of root exposure employing the "Envelope" technique. J. Periodontol. 1985; 56:397-402; two horizontal incisions only; Bruno J F. Connective tissue graft technique assuring wide coverage. Int. J. Periodontics Restorative Dent. 1994; 14:127-37; and the single incision technique; Hurzeler M B, Weng D. A single incision technique to harvest subepithelial connective tissue grafts from palate. Int J Periodontics Restorative Dent. 1999; 19:279-87.

The palatial connective tissue graft (CTG) is usually obtained through 2 incisions: vertical and horizontal. The vertical incision uses a blade perpendicular to the palatal tissue, and 2 to 3 mm away from the apical margin of the maxillary teeth. The horizontal incision follows the gingival margin, and the length is dependent on the required size to cover the exposed area, as well as depth for the elevation and removal of the donor tissue. The periodontal probe is the most common instrument used to gauge the depth of the soft tissue graft. It can help, as well, to measure the length up to 15 mm. Once the side is determined, a partial-thickness dissection is then made either through a single or double horizontal incision; Goldstein M, et al., A critical evaluation of methods for root coverage. Crit Rev Oral Biol Med. 1996; 7(1):87-98.

The dissection is performed based on the height of the palatal vault which could be high, medium or low, and it is extended as necessary to obtain the desired size of the graft. After removing the connective tissue graft carefully from the underlying periosteum with the elevator, it is recommended to suture the donor area to stop the bleeding and accelerate the healing process.

Another way to obtain an oral soft tissue graft is the free gingival graft (FGG). It is a superficial graft that contains mainly epithelium tissue and is obtained manually through horizontal and vertical incisions to the required depth and width in the palatal tissue and 2 to 3 mm away from the apical margin of the maxillary teeth; Butler B L. The subepithelial connective tissue graft with a vestibular releasing incision. J. Periodontol. 2003 June; 74(6):893-8; Camargo P M, et al. The use of free gingival grafts for aesthetic purposes. Periodontol 2000. 2001; 27:72-96.

The incisions of the FGG are made perpendicular to the gingival surface, creating a 90 degree angle. The final graft is a square or rectangle shape that can cover the desired recipient site. The periodontal probe can help to measure the depth and avoid any bone exposure which usually will cause a painful sensation to the patient.

The desired thickness of CTG or FGG is between 1 mm to 1.5 mm which can be measured by the periodontal probe. The recommended area of harvesting is the hard palate between the distal area of canine to the mid-palatal of the first maxillary molar or the maxillary tuberosity. The dimension of the graft is one and a half times bigger than the dimensions of the recipient area due to tissue shrinkage. Then, the fatty layer is removed to improve the blood supply and tissue stability; Zucchelli G, et al., Patient morbidity and root coverage outcome after subepithelial connective tissue and deep epithelialized grafts: a comparative randomized-controlled clinical trial. J Clin Periodontol. 2010b Aug. 1; 37(8):728-38; Zucchelli G, et al., Predetermination of root coverage. J Periodontol. 2010a July; 81(7):1019-26.

There are some factors which may complicate the harvesting process, such as the variability of graft thickness. Moreover, the actual thickness of the graft is usually about one millimeter, which is sometime difficult to obtain, or at risk of damage after graft adjustment.

Several attempts were suggested to improve graft harvesting such as a mucotome or a mucous membrane cutter; Gunay H, et al. Harvesting technique using a mucotome and modified surgical procedure for root coverage with enamel matrix derivatives with and without a connective tissue graft. Int J Periodontics Restorative Dent. 2008 October;

28(5):497-507; Grant, U.S. Pat. No. 4,240,432A. However, these devices cannot help to measure the thickness of the soft tissue. A periodontal probe on the other hand will help to measure the depth, but it can only measure a width up to 15 mm, which is not sufficient. In addition, there are only several types of periodontal probes, and some of them are difficult to use to obtain the actual depth. Moreover, the uneven surface of the palate presents a challenge in achieving a uniform thickness desirable for many tissue grafts.

Accordingly, these instruments still fail to assess the actual depth and width of the desired soft tissue grafts.

SUMMARY

A soft tissue caliper disclosed herein can harvest a soft tissue graft while accessing the depth and width of the graft at the same time. This can help to provide a uniform graft thickness. Moreover, it can measure the thickness of the tissue and set a cutting location to obtain a desired graft size.

The device in some embodiments can quickly, easily, and accurately provide viable grafts of uniform thickness for use in surgical procedures, especially in dental surgery. The instrument can be adjusted to provide grafts of different widths and thicknesses, and compared to manual procedures can provide a standardized desired thickness when used by different practitioners.

A soft tissue gauge, in one embodiment, can include a fixed probe for insertion into tissue to assess a depth of insertion of the fixed probe. The fixed probe can have a fixed probe depth indicator to determine the depth of insertion of the fixed probe. A movable probe for insertion into tissue can also be provided to assess a depth of insertion of the movable probe. The movable probe can have a movable probe depth indicator to determine the depth of insertion of the movable probe. A ruler can be provided having a fixed base supporting the fixed probe and a movable base supporting the movable probe. The movable base can have a sliding part allowing for adjustment of the movable probe along the ruler to a desired length.

The fixed probe depth indicator can be a color indicator in some embodiments.

The movable probe depth indicator can also be a color indicator.

Each of the fixed probe depth indicator and movable probe depth indicator can be colored grey at 1, 4, 7 mm, blue at 2, 5, 8 mm, and red at 3, 6, 9 mm in some embodiments.

The sliding part can include a button that fixes the movable base into position when pressed.

A soft tissue gauge, in an alternate embodiment, can include a fixed probe for insertion into tissue to assess a depth of insertion of the fixed probe. The fixed probe can have a color fixed probe depth indicator to determine the depth of insertion of the fixed probe. A movable probe for insertion into tissue can also be provided to assess a depth of insertion of the movable probe. The movable probe can have a color movable probe depth indicator to determine the depth of insertion of the movable probe. A ruler can be provided having a fixed base supporting the fixed probe and a movable base supporting the movable probe. The movable base can have a sliding part allowing for adjustment of the movable probe along the ruler to a desired length. The color fixed probe depth indicator and color movable probe depth indicator can be colored grey at 1, 4, 7 mm, blue at 2, 5, 8 mm, and red at 3, 6.9 mm.

The sliding part has a button that fixes the movable base into position when pressed.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

A soft tissue gauge with depth and length measurements is disclosed herein. The gauge in some embodiments is in the form of a caliper, with the ends of the caliper having stationary and movable color-coded needle-like probes. The probes are inserted in the tissue to assess the depth, with the movable probe placed at the desired length. Both probes are color-coded with gray bands at 1, 4, and 7 mm, blue bands at 2, 5, and 8 mm, and red bands at 3, 6, and 9 mm.

Figure 1:
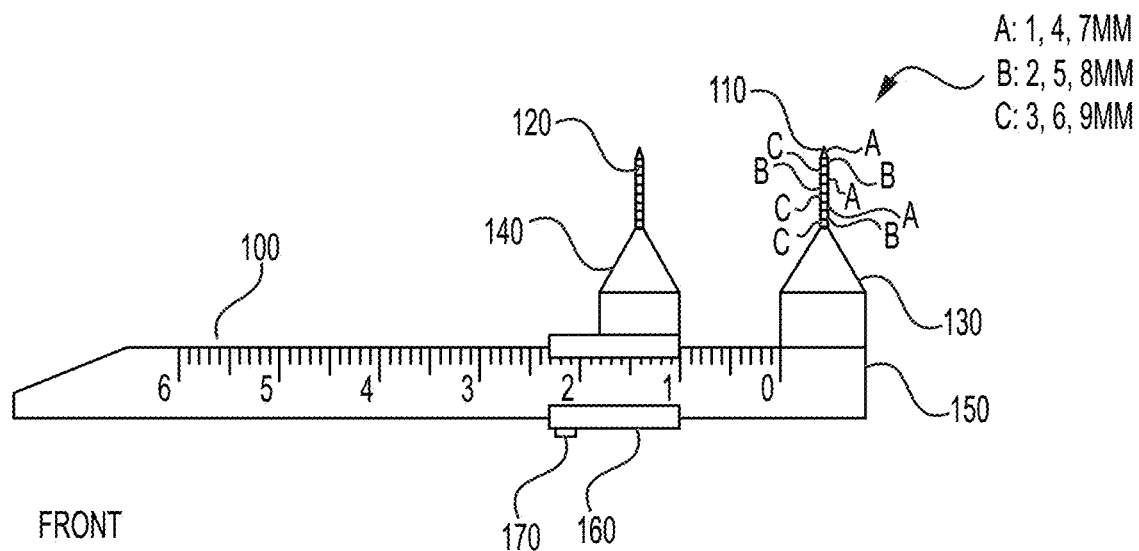
FIG. 1 is a front view of the soft tissue gauge described herein.
Figure 2:
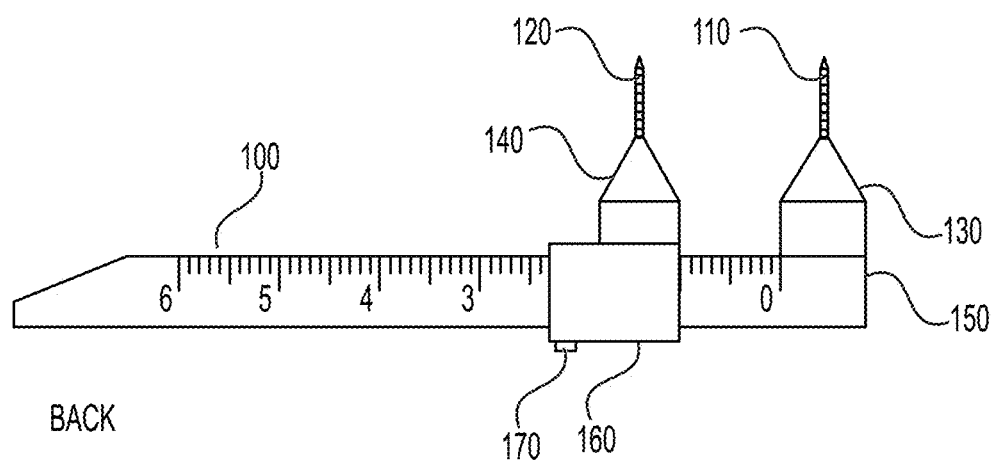
FIG. 2 is a back view of the soft tissue gauge described herein.

FIG. 1 and FIG. 2 are front and back views of a soft tissue gauge 100, respectively. The soft tissue gauge 100 includes a fixed colored probe 110, which will be inserted into the tissue to assess the depth of the soft tissue, and a movable color probe 120, which assesses the depth of the soft tissue and will be placed at the desired length. The length of each of the probes 110 and 120 is about 9 mm. Both probes 110 and 120 include a fixed and movable probe depth indicator. The indicators can be colored, grey at 1, 4, 7 mm; blue at 2, 5, 8 mm; and red at 3, 6, and 9 mm. Color coding the probes helps to identify the thickness of soft tissue once the probes 110 and 120 are inserted. Alternatively, the indicators could be markings such as lines on the probe. The markings could, in some embodiments, vary in thickness or be of different shapes to distinguish varying depths.

The fixed colored probe 110 is supported by fixed base 130 and movable color probe 120 is supported by movable base 140 which is linked to a ruler 150. The movable base 140 is linked to the ruler 150 by a sliding part 160 which allows for adjustment to a desired graft length. Once the desired length is determined, the movable base 140 can be fixed into position using button 170 of the sliding part 160.

In order to take a graft, in one embodiment, a graft site is initially selected. The fixed color probe 110 is placed over a selected graft site area. Movable color probe 120 is then moved using sliding part 160 over the graft site until a desired length is reached. Once a desired length is selected, button 170 is depressed to fix the movable color probe 120 into place. The fixed color probe 110 and the moveable color probe 120 are then pushed into the graft site until the desired depth is reached. For example, if the desired depth is 2 mm, then the fixed color probe 110 and the movable color probe 120 should be inserted into the graft site up to the first blue band which indicates 2 mm. The length and depth of the graft are now identified using the soft tissue gauge allowing a practitioner to now remove the graft.

The soft tissue gauge as described herein can be disposable or sterilizable, accurate, fast, easy to use, adjustable, and give a certain level of predictability and reproducibility. It can be used to measure the depth (thickness) of an area to obtain a desired thickness for connective tissue grafts, skin layers, mucus membrane, connective tissue, epithelium, Keratinized gingival, non-kertanized gingival, para-kertainized gingival, free gingival grafts, dermis, epidermis, membrane, barriers, etc. Other applications include measuring the width of a jaw, an amount of recession, a desired length of graft, periodontal pockets and bone sounding It is to be understood that the present subject matter is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A soft tissue gauge, comprising:
   a fixed probe configured for insertion into tissue to assess a depth of insertion of the fixed probe, the fixed probe having a fixed probe depth indicator to determine the depth of insertion of the fixed probe;
   a movable probe configured for insertion into the tissue to assess a depth of insertion of the movable probe, the movable probe having a movable probe depth indicator to determine the depth of insertion of the movable probe; and
   a ruler having a fixed base supporting the fixed probe and a movable base supporting the movable probe, the movable base having a sliding part allowing for adjustment of the movable probe along the ruler to a desired length, and wherein the movable base is linearly adjustable with respect to the fixed probe.

2. The soft tissue gauge as recited in claim 1, wherein the fixed probe depth indicator is a color indicator.

3. The soft tissue gauge as recited in claim 1, wherein the movable probe depth indicator is a color indicator.

4. The soft tissue gauge as recited in claim 1, wherein each of the fixed probe depth indicator and the movable probe depth indicator is colored grey at 1, 4 and 7 mm, blue at 2, 5 and 8 mm, and red at 3, 6 and 9 mm.

5. The soft tissue gauge as recited in claim 1, wherein the sliding part has a button that fixes the movable base into position when pressed.

6. A soft tissue gauge, comprising:
   a fixed probe configured for insertion into tissue to assess a depth of insertion of the fixed probe, the fixed probe having a color fixed probe depth indicator to determine the depth of insertion of the fixed probe;
   a movable probe configured for insertion into the tissue to assess a depth of insertion of the movable probe, the movable probe having a color movable probe depth indicator to determine the depth of insertion of the movable probe; and
   a ruler having a fixed base supporting the fixed probe and a movable base supporting the movable probe, the movable base having a sliding part allowing for adjustment of the movable probe along the ruler to a desired length,
   wherein the color fixed probe depth indicator and the color movable probe depth indicator are each colored grey at 1, 4 and 7 mm, blue at 2, 5 and 8 mm, and red at 3, 6 and 9 mm.

7. The soft tissue gauge as recited in claim 6, wherein the sliding part has a button that fixes the movable base into position when pressed.

\* \* \* \* \*